(12) United States Patent
Muenchau et al.

(10) Patent No.: US 7,215,738 B2
(45) Date of Patent: May 8, 2007

(54) METHOD AND SYSTEM FOR AUTOMATICALLY SCANNING AND IMAGING THE CONTENTS OF A MOVING TARGET

(75) Inventors: Ernest E. Muenchau, San Diego, CA (US); Rex D Richardson, Poway, CA (US)

(73) Assignee: Science Applications International Corporation, San Diego, CA (US)

( * ) Notice: Subject to any disclaimer, the term of this patent is extended or adjusted under 35 U.S.C. 154(b) by 0 days.

(21) Appl. No.: 11/370,883

(22) Filed: Mar. 9, 2006

(65) Prior Publication Data

US 2007/0071165 A1   Mar. 29, 2007

Related U.S. Application Data

(63) Continuation of application No. 10/767,723, filed on Jan. 30, 2004, now Pat. No. 7,039,159.

(51) Int. Cl.
    G01N 23/04    (2006.01)
    G21K 1/04     (2006.01)

(52) U.S. Cl. .............. 378/57; 378/160; 250/505.1

(58) Field of Classification Search ............ 378/57, 378/160; 250/505.1
    See application file for complete search history.

(56) References Cited

U.S. PATENT DOCUMENTS

| | | | | |
|---|---|---|---|---|
| 3,390,269 A | * | 6/1968 | Packard | 250/328 |
| 3,829,695 A | * | 8/1974 | Powell | 250/358.1 |
| 4,946,256 A | * | 8/1990 | Woodruff | 359/230 |
| 5,834,780 A | * | 11/1998 | Morgan et al. | 250/363.04 |
| 5,986,275 A | * | 11/1999 | Teates | 250/498.1 |
| 6,031,890 A | | 2/2000 | Bermbach et al. | 378/57 |
| 6,255,654 B1 | | 7/2001 | Verbinski et al. | 250/358 |
| 6,400,795 B2 | | 6/2002 | Yagi | 378/45 |
| 6,507,025 B1 | * | 1/2003 | Verbinski et al. | 250/358.1 |
| 6,552,346 B2 | | 4/2003 | Verbinski et al. | 250/358.1 |

(Continued)

OTHER PUBLICATIONS

International Search Report and Written Opinion for Application No. PCT/US04/31725, dated Sep. 30, 2005 (mailing date).

*Primary Examiner*—Edward J. Glick
*Assistant Examiner*—Thomas R. Artman
(74) *Attorney, Agent, or Firm*—Kilpatrick Stockton LLP

(57) ABSTRACT

The system and method described herein facilitate back-to-back automatic scanning of moving vehicles without have the vehicles stop in the scanning zone. The system includes a scanning zone that comprises a radiation source and a radiation source detector. The system further includes a first sensor component for automatically sensing when a first portion of the moving target has passed through the scanning zone and a second portion of the moving target is about to enter the scanning zone, wherein the first sensor component sends a signal to the automated target inspection system to initiate a scan of the second portion upon sensing that the second portion of the target is about to enter the scanning zone. Additionally, a shutter, triggered by a signal from the first sensor component, allows radiation from the radiation source to pass through the scanning zone in the direction of the radiation detector when the second portion of the moving target is passing through the scanning zone and closes off the radiation when the second portion of the moving target is no longer within the scanning zone.

18 Claims, 5 Drawing Sheets

U.S. PATENT DOCUMENTS 6,649,906 B2 * 11/2003 Adolph et al. ........... 250/269.1
7,039,159 B2 * 5/2006 Muenchau et al. ........... 378/57
7,045,788 B2 * 5/2006 Iwatschenko-Borho et al. . 250/359.1
7,046,768 B1 * 5/2006 Gilevich ..................... 378/160

* cited by examiner

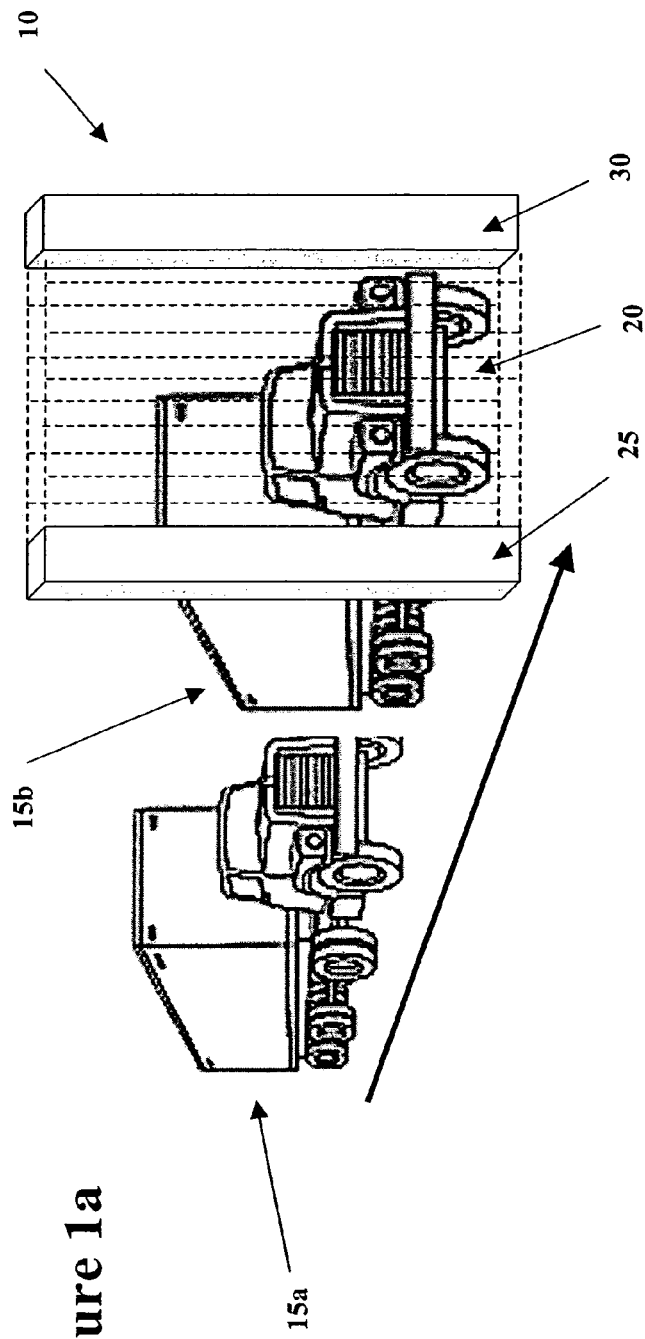
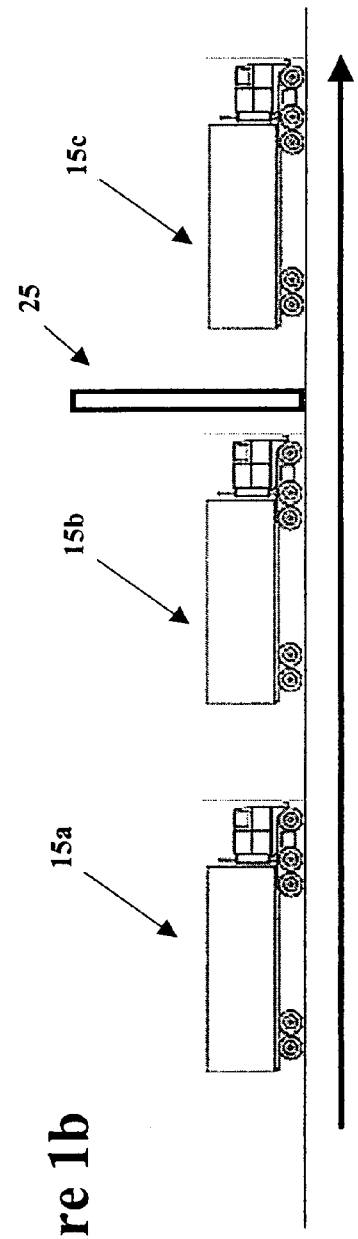
Figure 1a
Figure 1b

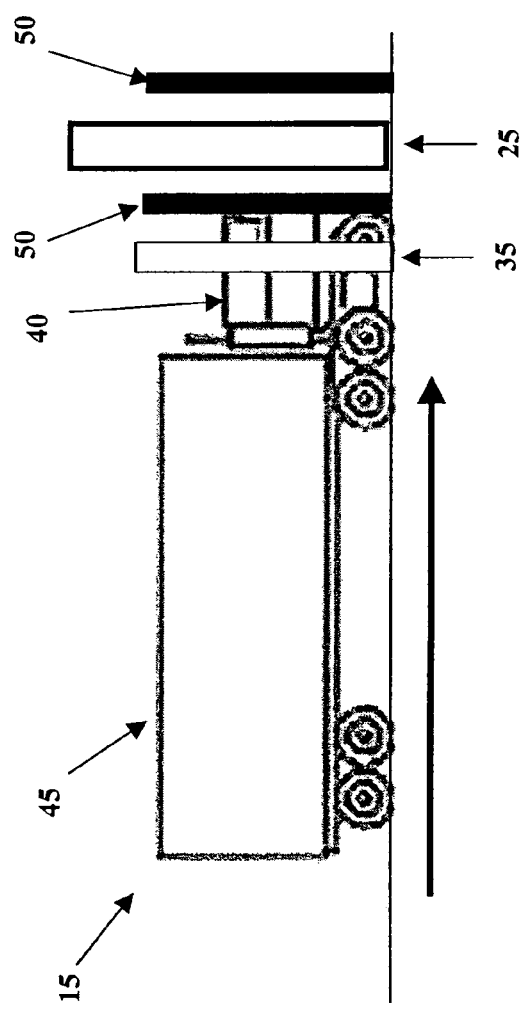
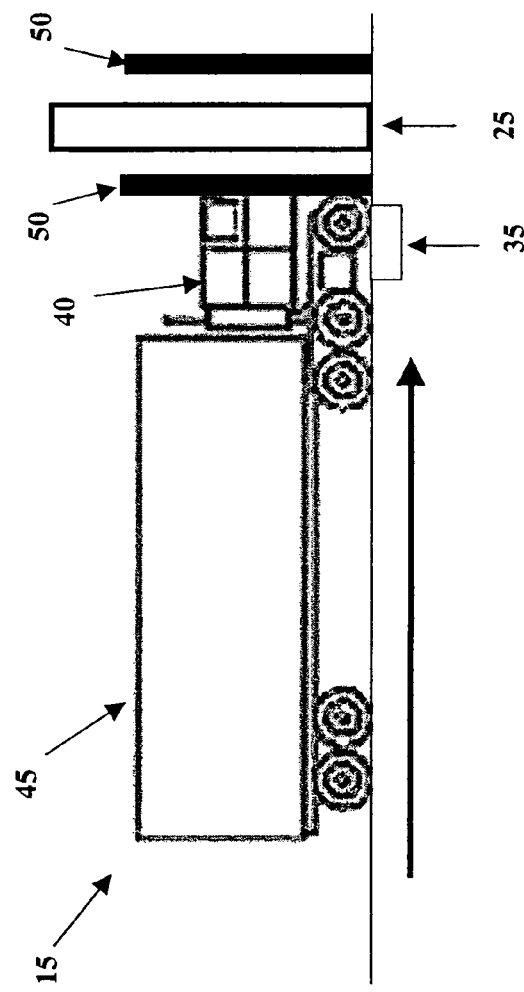

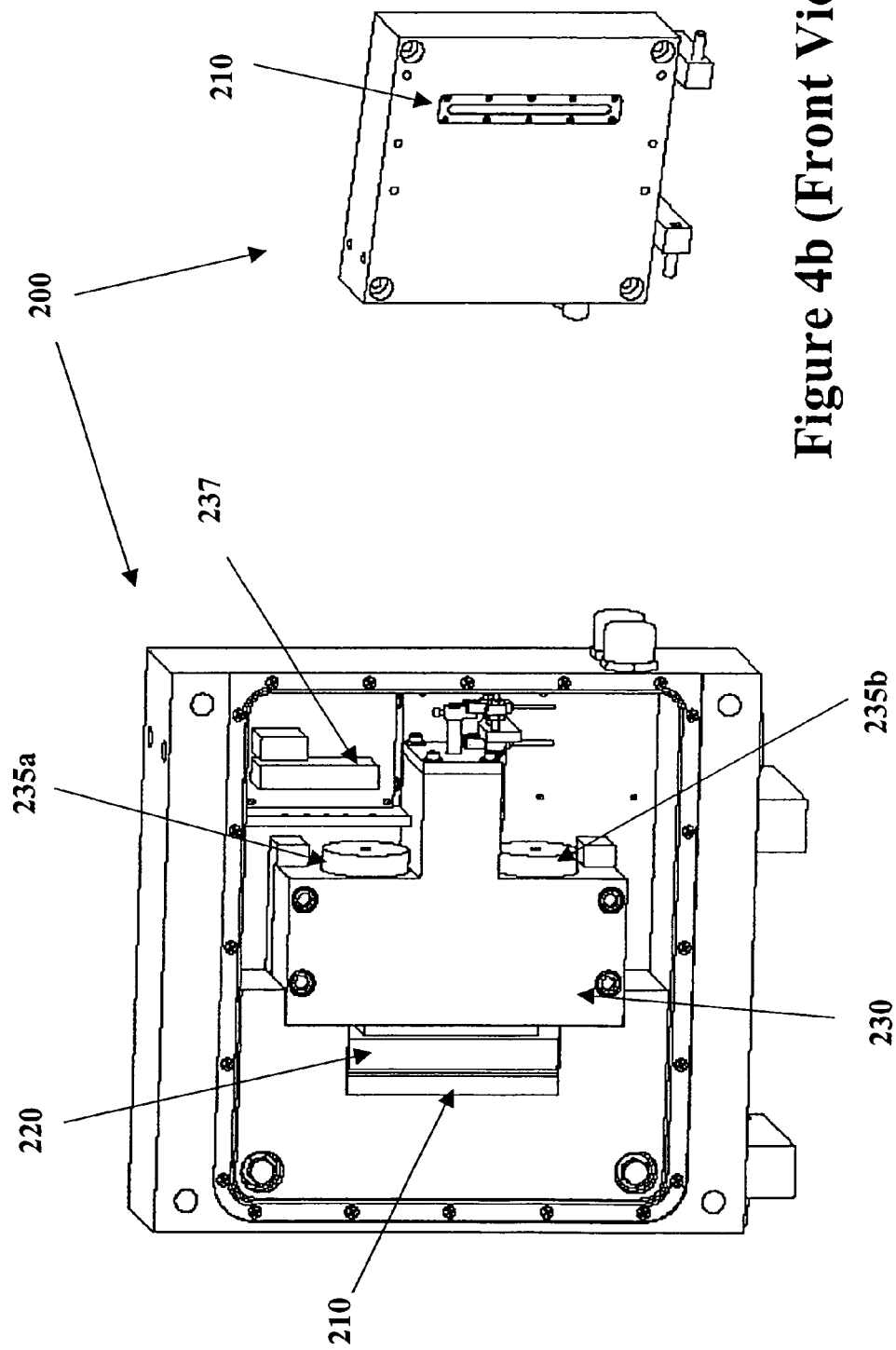

METHOD AND SYSTEM FOR AUTOMATICALLY SCANNING AND IMAGING THE CONTENTS OF A MOVING TARGET

CROSS-REFERENCE TO RELATED APPLICATIONS

This application is a continuation of and claims priority to U.S. patent application Ser. No. 10/767,723 entitled METHOD AND SYSTEM FOR AUTOMATICALLY SCANNING AND IMAGING THE CONTENTS OF A MOVING TARGET filed Jan. 30, 2004 now U.S. Pat. No. 7,039,159, which is incorporated herein by reference in its entirety.

BACKGROUND OF THE INVENTION

1. Field of the Invention

The invention relates generally to the field of imaging a target and more particularly to the field of imaging the contents of a moving target.

2. Description of the Related Art

In this time of increased security concerns, authorities are continually looking for ways to improve national security through imaging technology. Additionally, law enforcement continues to battle drug, stolen goods and people trafficking both at the borders and within the borders of the United States through nonintrusive x-ray and gamma-ray imaging. There is a balance that must be struck between the desire to check the contents of vehicles for illegal and/or potentially hazardous materials and the desire to protect the drivers of the vehicles and to minimize the impact of the investigation on the flow of commerce.

Currently available vehicle and cargo imaging systems, particularly those directed towards the imaging of moving targets, i.e., trucks, etc., utilize stop-and-go procedures that require manual control of the scan process. For example, current systems require the driver of the moving target to (1) stop the vehicle in a scanning zone, (2) certain systems require the driver to exit the vehicle and go a safe distance from the scanning zone to avoid potential exposure to the imaging radiation and, (3) certain systems require the driver, or some third party, to manually initiate the scanning of the vehicle. Further, many of the systems that are currently available for such imaging, utilize a high power x-ray source for the imaging radiation.

By way of specific example, a particular known vehicle and cargo imaging system and process is described as follows. The driver approaches the first of 3 traffic signals. The first signal "enter" is green when there is no vehicle sensed between opposing source and detector towers defining the scan area, and red when there is a vehicle in the scan area. When the "enter" signal turns green the driver approaches a driver arm and the second traffic signal, which is red at this point. The "enter" of the first traffic signal also turns red, prohibiting any other vehicles from entering the scan area. Sensors detect the presence of the vehicle and a flashing yellow light on the driver arm engages. This prompts the driver to press the driver pushbutton located on a panel outside of the vehicle before the driver arm. This pushbutton sends a signal to an operator console notifying the operator that the driver is ready for his vehicle to be scanned. The operator presses the blinking "scan" button on the operator console and the shutters to the scanning source are opened. At this time, the second "scan" traffic light turns green and the driver proceeds through the scan area. As the vehicle exits the scan area, sensors detect the lack of a vehicle and automatically close the shutters to the scanning source. At this point, the first "enter" traffic signal turns green for another vehicle to proceed to the driver arm. Lastly, the "Exit" button on the operator panel lights up and the operator can depress the button to change the third traffic signal from red to green, thus allowing the vehicle to completely exit the area. This whole process takes approximately 20 seconds for a nominal scan.

SUMMARY OF THE INVENTION

Summary of the Problem

Referring to the "Description of the Related Art," there is a need for a system and method to automatically scan and image moving vehicles in an optimally efficient and unobtrusive manner so as to minimize the effect on the flow of commerce and protect the drivers and third parties from exposure to the scanning radiation.

Summary of the Solution

The present invention describes a system and method for automatically scanning a target vehicle according to at least the following embodiments.

According to a first embodiment of the present invention, described herein is an automated target inspection system for inspecting a moving target. The system includes a scanning zone that comprises a radiation source and a radiation source detector. The system further includes a first sensor component for automatically sensing when a first portion of the moving target has passed through the scanning zone and a second portion of the moving target is about to enter the scanning zone, wherein the first sensor component sends a signal to the automated target inspection system to initiate a scan of the second portion upon sensing that the second portion of the target is about to enter the scanning zone. Additionally, a shutter, triggered by a signal from the first sensor component, allows radiation from the radiation source to pass through the scanning zone in the direction of the radiation detector when the second portion of the moving target is passing through the scanning zone and closes off the radiation when the second portion of the moving target is no longer within the scanning zone.

According to a second embodiment of the present invention, described herein is a method for automatically inspecting a moving target with an automated target inspection system. The method includes (1) sensing when a first portion of the moving target has passed through a scanning zone and a second portion of the moving target is about to enter the scanning zone; (2) sending a signal to the automated target inspection system to initiate a scan of the second portion upon sensing that the second portion of the target is about to enter the scanning zone; (3) opening a shutter to allowing radiation from a radiation source to pass through the scanning zone in the direction of a radiation detector when the second portion of the moving target is passing through the scanning zone; and (4) closing the shutter to shut off the radiation when the second portion of the moving target is no longer within the scanning zone.

According to a third embodiment of the present invention, described herein is a system for automatically inspecting a moving target. The system includes means for sensing when a first portion of the moving target has passed through a scanning zone and a second portion of the moving target is about to enter the scanning zone; means for sending a signal to the automated target inspection system to initiate a scan of the second portion upon sensing that the second portion of the target is about to enter the scanning zone; means for opening a shutter to allowing radiation from a radiation source to pass through the scanning zone in the direction of a radiation detector when the second portion of the moving target is passing through the scanning zone; and means for closing the shutter to shut off the radiation when the second portion of the moving target is no longer within the scanning zone.

BRIEF DESCRIPTION OF THE FIGURES

In the Figures:

FIG. 1a is a first view of a non-stop automatic scan system according to an embodiment of the present invention;

FIG. 1b is a second view of a non-stop automatic scan system according to an embodiment of the present invention;

FIG. 3a shows a non-stop automatic scan system with a first start/stop sensor configuration according to an embodiment of the present invention;

FIG. 3b shows a non-stop automatic scan system with a second start/stop sensor configuration according to an embodiment of the present invention;

FIG. 4a is a first view of a shutter mechanism according to an embodiment of the present invention;

FIG. 4b is a second view of a shutter mechanism according to an embodiment of the present invention.

DETAILED DESCRIPTION OF THE PREFERRED EMBODIMENTS

Figure 2:
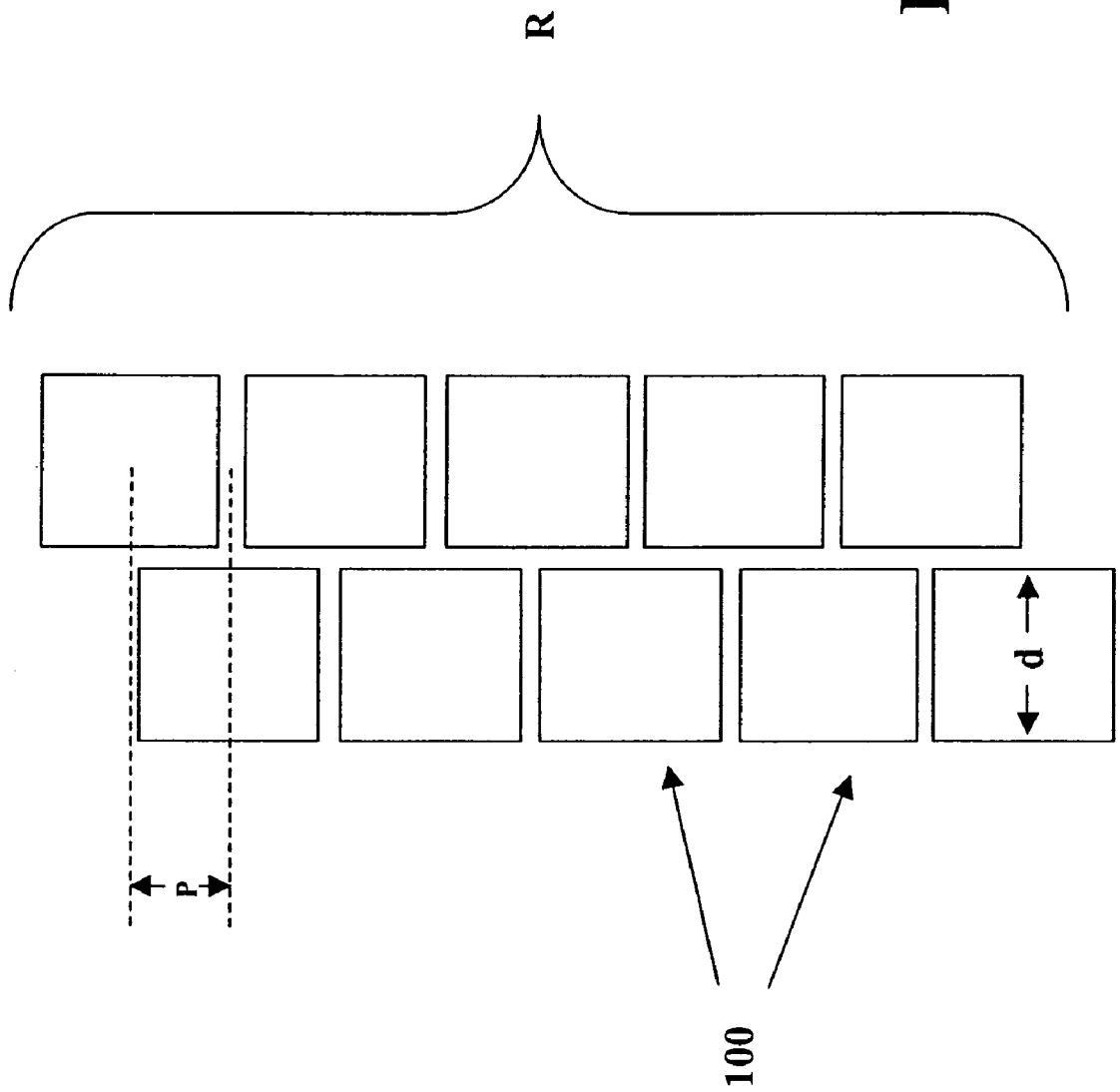
FIG. 2 shows a detector configuration according to an embodiment of the present invention.

In addition to the description set forth explicitly below, numerous details and descriptions for various aspects of the preferred embodiments are set forth in the following United States patents and patent applications which are incorporated herein by reference in their entireties: U.S. Pat. No. 6,255,654 for DENSITY DETECTION USING DISCRETE PHOTON COUNTING; U.S. Pat. No. 6,507,025 for DENSITY DETECTION USING REAL TIME DISCRETE PHOTON COUNTING FOR FAST MOVING TARGETS; U.S. Pat. No. 6,552,346 for DENSITY DETECTION USING DISCRETE PHOTON COUNTING; U.S. patent application Ser. No. 09/925,009, for DENSITY DETECTION USING REAL TIME DISCRETE PHOTON COUNTING FOR FAST MOVING TARGETS, filed Aug. 9, 2001; and U.S. patent application Ser. No. 10/717,632 for DENSITY DETECTION USING REAL TIME DISCRETE PHOTON COUNTING FOR FAST MOVING TARGETS, filed Nov. 21, 2003.

Referring to FIGS. 1a and 1b, a preferred embodiment of the present invention provides a non-stop drive-through scanning system 10 for imaging the contents of moving target vehicles, e.g., 15a, 15b, 15c, etc. (referred to herein individually as 15). The preferred embodiments of the present invention facilitate back-to-back scanning of moving vehicles 15a, 15b, 15c, etc., without the need to stop the vehicle and initiate scanning manually, thus facilitating increased rate of the flow of commerce. The system of FIGS. 1a and 1b allows the driver of a vehicle, e.g., van, truck, train, etc. to enter the scanning zone 20 without the need to stop or exit from the target vehicle 15. The scanning zone 20 is defined by the space between opposing source and detector towers 25, 30. Details regarding various embodiments of the source and detector towers are described in the patents and applications listed above which are incorporated herein by reference. By way of example, the source tower 25 may include a radiation source such as a $3.7 \times 10^{10}$ Bq shuttered source of Cs-137 gamma-rays, i.e., 662 keV gamma-ray energy. In an alternative embodiment, a Co-60 source may be used. A suitable source is readily available as Model Nos. SH-F-2 and SH-F-3 from Ohmart Corporation of Ohio. The radiation source may include a collimator that provides desired vertical and lateral opening specifications.

The radiation source provides gamma-rays that are only moderately attenuated by steel walls typically found in tanker trucks or railroad cars. Yet such rays are sufficiently attenuated by contraband packages to make them easily detectable by measuring the penetration of the gamma-rays emitted from the source and deriving relative material densities therefrom. In addition, there is negligible scattering of the gamma-ray energy from the tanker walls or cargo, much less than would occur if a high-powered x-ray source was utilized.

An exemplary detector tower 30 includes a detector array that employs a plurality of high efficiency gamma-ray detectors, e.g., between twenty and sixty, e.g., forty-eight, detectors arranged in a vertical column. The detectors make it possible to scan the target vehicle with a very low intensity gamma-ray field. In order to facilitate the use of very low intensity gamma-radiation, high efficiency detectors are used, such as are available as Part No. 1.5M1.5M1.5, NaI (TI) (sodium iodide crystal, thallium activated) (with R2060 photomultiplier tube) from BICRON of Ohio. Such gamma-ray detectors are scintillation counter-type detectors and are 3.8 cm in diameter, 3.8 cm high and mounted on a 3.8 cm photo-multiplier tube (PMT).

Alternatively, 1.125" (2.858 cm) square detectors may be used with the number of detectors used in the detector configuration ranging between 40 and 180, depending on desired resolution requirements. Referring to FIG. 2, in a specific embodiment, the detector array includes a plurality of staggered NaI/PMT square photon detector elements 100. Each individual detector is 1.125" (2.858 cm) square and has a pitch P smaller than the diameter (d) of the staggered detector elements 100. Two (2) vertical rows R of staggered detector elements 100 are employed, instead of a single row of detectors. The two (2) vertical rows R are vertically staggered from each other. The pitch P between two (2) closest adjacent such staggered detector elements 100 may preferably be about 0.7", when employing staggered detector elements 100 having a 1.125" (2.858 cm) diameter, thereby yielding a count rate of about 95,000 counts/second for each staggered detector element for D=16 feet and for a 1.0 Curie Cs-137 source. By way of example, this pitch P results in a vertical resolution, $R_{vert}$ or vertical grid unit of about 0.23" when the radiation source is a distance D of 16 feet from the staggered detector element and the radiation source is a distance z of 8 feet (2.4 meters) from a center of the moving target vehicle wherein $R_{vert}=PZ/D$.

The staggered detectors are staggered from each other in a vertical direction, yet their surfaces of each vertical row all lie in a same plane, thereby avoiding shadowing from any other staggered detector while enabling a smaller pitch P.

Referring to FIGS. 3a and 3b, at least one start/stop sensor 35 is located prior to the scanning zone and is used to determine when the cab or driver/passenger area 40 (hereafter "cab") has cleared the scanning zone and the payload 45 of the target vehicle 15 is entering the scanning zone. Once the start/stop sensor 35 senses the payload 45 has entered, or is about to enter, the scanning zone, the non-stop system initiates an automatic scan. The start/stop sensor 35 may include at least one of optical, electrical, pressure, video technology or the like for determining the start/stop points and automatic scan initiations as described above. More particularly, and by way of example, sensor technologies may be employed to count axles and/or measure the space between the cab 40 and the payload 45. In FIG. 3a, the at least one start/stop sensor 35 is located prior to the scanning zone and is above the level of the driving surface. In an alternative embodiment shown in FIG. 3b, the start/stop sensor 35 is located within or very near to the driving surface. In this embodiment, the sensor may be outside of the driving lane or actually in the driving lane such that the target vehicle is driven directly over the start/stop sensor 35. One skilled in the art can appreciate the various sensor configurations that would be considered to be within the scope of the present invention.

Figure 4C:
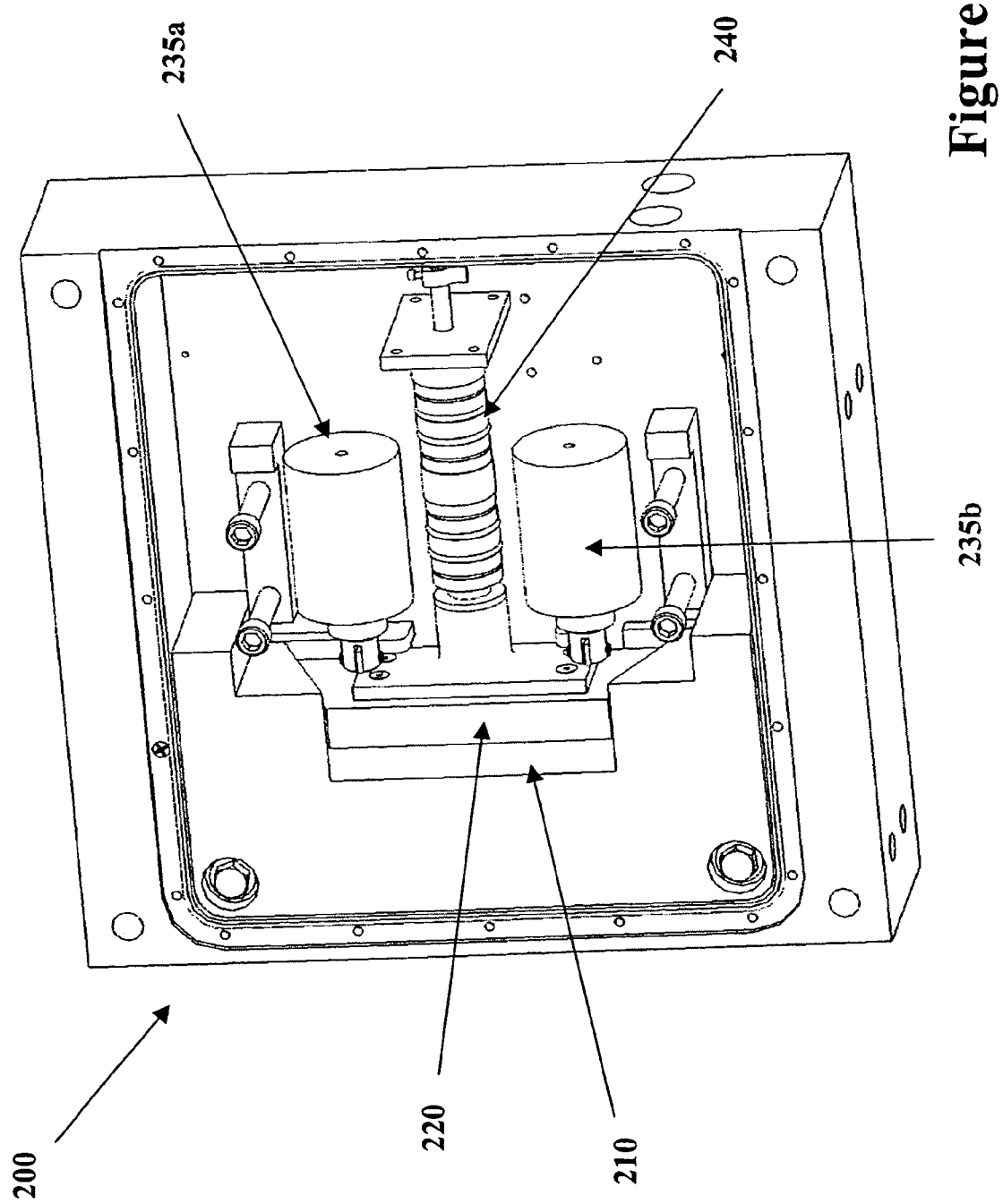
FIG. 4c is a third view of a shutter mechanism according to an embodiment of the present invention.

Referring to FIGS. 4a–4c, in an embodiment of the present invention the automatic initiation of a scan includes, among other features, controlling a shutter assembly, including a fast shutter mechanism 200 located in the source tower that allows at least a first fast shutter to open and allow radiation from the radiation source to exit through beam aperture 210 in a sufficient time, e.g., on the order of a few tens of milliseconds, between detection of the cab and the payload by the start/stop sensor, so as to allow for a complete payload scan, i.e., including the beginning edge of the payload, while the target vehicle is moving, i.e., at speeds of up to 10 miles per hour, with normal operating range of between 5–10 mph. By way of particular example, the system and method of the present invention facilitates a fast shutter opening time on the order of 50 milliseconds or less, preferably 40 milliseconds, to allow the shutter to fully open after the cab passes the start/stop sensor when a target vehicle driving at 7 MPH proceeds through the non-stop system. Further, based on the data from start/stop sensor, the fast shutter mechanism is controlled so as to close the at least one shutter at the end of the payload, before a second target vehicle enters the scanning zone. The time for the fast shutter to close is, for example, on the order of no less than 100 milliseconds, preferably on the order of 350 milliseconds. The latter closing time reflects a desired traffic pattern of vehicles allowing for at least 15 feet of separation between the payload trailing edge and the leading edge of the next target vehicle.

The fast shutter mechanism utilizes at least one linear sliding shielding block 220 driven by an electromagnetic pulse actuated by a solenoid assembly 230. When this shutter is closed, the shutter shielding block 220 operates to attenuate the radiation source. i.e., gamma source, to within acceptable exposure levels. In both the open and closed position, the configuration of the shutter shielding block 220 provides shielding of off-axis radiation exiting from the source assembly. In a preferred embodiment, the shutter shielding block comprises tungsten, with a thickness of approximately 2.4 inches (6.1 cm). An exemplary solenoid assembly 230 includes two electromechanical solenoids 235a and 235b operating together and control by solenoid drive electronics 237 to pull the shutter to the open position. The solenoids 235a and 235b are sized to open the shutter and allow radiation from the radiation source to exit through beam aperture 210 independently in the case of the failure of the other. This design, though resulting in a slightly slower shutter opening time, avoids system shut down altogether. And as described further below, shutter diagnostics will report the solenoid failure, i.e., the slower than normal opening time to the shutter mechanism control system and alert operators to the need for repair. Referring to FIG. 4c, a return spring 240 is used to close the fast shutter 210 in response to the start/stop sensor sensing the end of the payload. The return spring 240 is sized to provide enough energy to close the shutter in less than approximately 350 milliseconds, yet not provide excess force required to open the shutter 210.

Additionally, as shown in FIGS. 3a and 3b, the non-stop system may include at least one radiation sensor 50, such as at least one rate meter, for sensing the levels of radiation, i.e., gamma or x-ray, outside of the confines of the scanning zone 20 as a protective measure. An alarm or other indication mechanism is triggered by at least one radiation sensor 50 to alert drivers, passengers, and other $3^{rd}$ parties to the potential for radiation exposure in the area around each scanning zone 20.

The shutter assembly described herein with respect to the preferred embodiments of the present invention also includes a failsafe operating design, wherein the at least one shutter fails in a closed condition, thus ensuring safety from possible radiation exposure in the event of, for example, a system power failure, a system error, or shutter failure. Further, the control system for the shutter assembly includes safety interlocks. For example, a key switch is used to control access to the shutter controls. The primary shutter must be opened by an operator through a pushbutton and the secondary, i.e., fast, shutter, must be enabled through a pushbutton. The portal system must be functional and enabled for operation. Emergency stops de-energize both the primary and secondary shutters directly in the event of an operator initiated emergency stop condition. The control system indicates shutter status to an operator through open/close status sensors. In order to maintain desired operation conditions, shutter diagnostics are incorporated into the control system and shutter assembly to report shutter failure status by providing error signals for the following failure conditions: shutter opening time exceeds preset value; shutter closing time exceeds preset value; shutter in transit, i.e., not in closed or open position; shutter current exceeds preset value; and shutter temperature exceeds preset temperature. The latter is measured as the output of a solenoid field effect transistor switch temperature sensor.

At least part of the source radiation from the radiation tower is detected by the detector array within the detector tower for imaging the contents of the target vehicle through a process of discrete photon counting. This process is described in detail in each of the patents and applications that have been incorporated herein by reference. By way of example, showing the detectors from the detector array are coupled through, for example, 16-channel processing units, RS-485 line drivers, and an RS-485 interface card to a computer, wherein the computer processes discrete photon count information received from the detectors and causes a display device to display an image of the contents of a target vehicle, in response thereto. In this particular example, the detectors are coupled in groups of 16 to 16-channel data processing circuits. Preferably, twenty (20) groups of detectors are used. In practice, the number of detectors used is variable depending on the height of the vehicles to be inspected and the resolution, i.e., number of pixels, in the image desired. In a preferred embodiment, 320 detectors are used. The data processing circuits, of which there are preferably twenty (2), are each coupled to an RS-485 line driver, which is coupled to an RS-485 interface. The RS-485 interface is embodied on a circuit card located within a computer system. A suitable RS-485 interface is available as Model No. 516-485, Part No. 3054 from Seal Level Systems, Inc., and from numerous other vendors under respective model/part number designations.

Each of the radiation detectors is coupled to a preamplifier within the 16-channel data processing circuits. Each preamplifier is coupled to an amplifier, which is in turn coupled to a discriminator. Each discriminator is coupled to a pulse generator, which generates an electrical pulse for each photon received into the radiation detector coupled thereto. The pulse generators within each of the 16-channel data processing circuits is coupled to a line driver. Each of the 16-channel data processing circuits includes its own line driver. The line drivers operate under the programmatic control of a firmware operating system. In operation, the preamplifiers, and amplifiers function in a conventional manner to amplify signals generated by the detectors. Outputs of the amplifiers are passed along to the discriminators, which impose a noise threshold on the amplified signal. Waveforms within the amplified signal that exceed the noise threshold are passed along to the pulse generator, which generates a pulse for each waveform within the amplified signal corresponding to a received gamma-ray or x-ray photon. The line driver passes the pulses generated by each of the pulse generators within a particular 16-channel data processing circuit along to the computer system via the RS-485 interface.

The computer system operates programmatically under the control of a software system. The computer system receives detector pulses from each of the 16-channel data processors, in response to the detection of individual photons by the detectors. The software system processes the incoming detector pulses, evaluating their relative amplitudes, i.e., energies, and generates a radio graphic image-like display output signal in response thereto. The radio graphic, image-like display output signal is coupled to the graphical display device and is used by the graphical display device to generate a graphical representation of the densities within the vehicle under inspection.

In summary, the system described herein is utilized to generate a graphical representation, i.e., a "picture", of the densities of the contents of the target vehicle. Advantageously, this allows for easy visual interpretation of the results of the scanning of the target vehicle under inspection, as opposed to interpreting more subtle indications of the densities within the vehicle under inspection as may be required in prior art systems. The preferred imaging software system causes the display of a reference image simultaneous with the image generated in response to the target vehicle under inspection, so that an operator of the present embodiment can easily make a visual comparison between what a vehicle of the same type or having the same type of cargo being inspected should "look like", and what the vehicle and cargo under inspection actually "looks like". Such side-by-side inspection further simplifies the detection of contraband using the present embodiment.

The embodiments and descriptions set forth herein are intended to be exemplary and not inclusive. One skilled in the art recognizes the numerous variations and equivalent components that may be used in accordance with the described invention and this fall within the scope thereof.

We claim:

1. An automated target inspection system for inspecting a moving target comprising:
    a scanning zone comprising a radiation source and a radiation source detector;
    a first sensor component for automatically sensing when a first portion of the moving target has passed through the scanning zone and a second portion of the moving target is about to enter the scanning zone, wherein the first sensor component sends a signal to the automated target inspection system to initiate a scan of the second portion upon sensing that the second portion of the target is about to enter the scanning zone; and
    a shutter, wherein the shutter comprises at least one shielding block driven by a dual solenoid configuration, triggered by a signal from the first sensor component for allowing radiation from the radiation source to pass through the scanning zone in the direction of the radiation source detector when the second portion of the moving target is passing through the scanning zone and for closing off the radiation when the second portion of the moving target is no longer within the scanning zone.

2. The system of claim 1, wherein the first sensor component senses a gap between the first portion of the moving target and the second portion of the moving target.

3. The system of claim 1, further comprising a spring for closing the shutter once the first sensor component senses that the first portion of the moving target is no longer within the scanning zone.

4. The system of claim 1, further comprising a radiation sensor component for sensing radiation from the radiation source that is outside of the scanning zone.

5. The system of claim 4, wherein the radiation sensor component is coupled to the shutter and further wherein the shutter is automatically closed in response to a radiation signal from the radiation sensor component.

6. The system of claim 1, further comprising a photon counter for counting photons comprising the radiation from the radiation source after the photons have passed through the moving target.

7. A method for automatically inspecting a moving target with an automated target inspection system comprising:
    sensing when a first portion of the moving target has passed through a scanning zone and a second portion of the moving target is about to enter the scanning zone;
    sending a signal to the automated target inspection system to initiate a scan of the second portion upon sensing that the first portion of the target is about to enter the scanning zone;
    opening a shutter comprising at least one shielding block driven by a dual solenoid configuration to allow radiation from a radiation source to pass through the scanning zone when the second portion of the moving target is passing through the scanning zone; and
    closing the shutter to shut off the radiation when the second portion of the moving target is no longer within the scanning zone.

8. The method of claim 7, wherein the shutter opening time is on the order of approximately 40 milliseconds.

9. The method of claim 7, wherein the shutter closing time is on the order of approximately 100–350 milliseconds.

10. The method of claim 7, further comprising sensing radiation that is outside of the scanning zone.

11. The method of claim 7, wherein opening the shutter includes moving the at least one shielding block to expose the radiation source.

12. The method of claim 11, wherein moving the at least one shielding block to expose the radiation source includes addressing a each solenoid within the dual solenoid configuration.

13. The method of claim 7, wherein closing the shutter includes activating a spring.

14. The method of claim 7, further comprising counting photons comprising the radiation from the radiation source after the photons have passed through the moving target.

15. The method of claim 14, further comprising imaging the second portion of the moving target based on density data determined from the photon counting.

16. An automated target inspection system for inspecting a moving target comprising:

a scanning zone including a gamma radiation source and a gamma radiation source detector;

a first sensor component for automatically sensing when a first portion of the moving target has passed through the scanning zone and a second portion of the moving target is about to enter the scanning zone, wherein the first sensor component sends a signal to the automated target inspection system to initiate a scan of the second portion upon sensing that the second portion of the target is about to enter the scanning zone; and a shutter, wherein the shutter comprises at least one shielding block driven by a dual solenoid configuration, triggered by a signal from the first sensor component for allowing gamma radiation from the gamma radiation source to pass through the scanning zone in the direction of the gamma radiation source detector when the second portion of the moving target is passing through the scanning zone and for closing off the gamma radiation when the second portion of the moving target is no longer within the scanning zone.

17. The system according to claim 16, wherein the moving target is moving at approximately 5–10 mph.

18. The system according to claim 16, wherein the gamma radiation from the gamma radiation source has an energy of approximately 667 keV.

* * * * *